United States Patent [19]
DeLuca et al.

[11] Patent Number: 4,719,204
[45] Date of Patent: Jan. 12, 1988

[54] FOWL BONE MINERALIZATION WITH 28-NOR 1α-HYDROXYVITAMIN $D_2$ ANALOGS

[75] Inventors: Hector F. DeLuca; Heinrich K. Schnoes, both of Madison, Wis.; Rafal R. Sicinski, Warsaw, Poland; Yoko Tanaka, Delmar, N.Y.

[73] Assignee: Wisconsin Alumni Research Foundation, Madison, Wis.

[21] Appl. No.: 784,142

[22] Filed: Oct. 3, 1985

Related U.S. Application Data

[63] Continuation of Ser. No. 586,160, Mar. 5, 1984, abandoned.

[51] Int. Cl.[4] ............................................. A61K 31/59
[52] U.S. Cl. ................................................... 514/167
[58] Field of Search ...................... 260/397.2; 514/167

[56] References Cited

U.S. PATENT DOCUMENTS 4,225,596  9/1980  DeLuca ............................... 514/167
4,508,651  4/1985  Baggiolini et al. ............... 260/397.2
4,554,105  11/1985  Hesse ................................ 260/397.2

Primary Examiner—Leonard Schenkman
Assistant Examiner—Joseph A. Lipovsky
Attorney, Agent, or Firm—Howard W. Bremer

[57] ABSTRACT

The invention provides, as novel vitamin D derivatives, analogs of vitamin $D_2$ compounds which lack the 24-methyl substituent and are identified as 1α-hydroxy-28-norvitamin $D_2$ and 1α,25-dihydroxy-28-norvitamin $D_2$.

The compounds of the invention are characterized by unexpectedly high vitamin D-like activity as well as a novel activity pattern. Because of such activity they would find ready application as substitutes for vitamin D or various of the known vitamin D metabolites in their various application for the treatment of calcium disorders.

3 Claims, No Drawings

FOWL BONE MINERALIZATION WITH 28-NOR 1α-HYDROXYVITAMIN D₂ ANALOGS

This invention was made with Government support under NIH Grant Nos. AM 14881 and AM 32701 awarded by the Department of Health and Human Services. The Government has certain rights in this invention.

This application is a continuation of application Ser. No. 586,160, filed Mar. 5, 1984, now abandoned.

TECHNICAL FIELD

The invention relates to biologically active vitamin D compounds. More specifically, this invention relates to 1α-hydroxyvitamin $D_2$ analogs which exhibit unexpected biological properties.

BACKGROUND

Because of the well-known and clearly established activity of 1α-hydroxyvitamin D compounds in regulating calcium and phosphate homeostasis in the animal or human, there has been interest in the preparation of the natural metabolites and in the discovery of analogs with useful biological properties. This has led to the preparation of a variety of compounds exhibiting biological activity (for examples, see DeLuca et al., Topics in Current Chem., vol. 83, p. 1 (1979); Ann. Rev. Biochem. 52, 411 (1983); Yakhimovich, Russian Chem. Rev. 49, 371 (1980)). Interest in such compounds in continuing especially now that it has been recognized that in addition to their classical function as regulators of calcium homeostasis, certain vitamin D derivatives, specifically, 1α,25-dihydroxyvitamin $D_3$ and 1α-hydroxyvitamin $D_3$, also affect cellular differentiation processes and are capable of inhibiting the growth and proliferation of certain leukemic cells [Suda et al., U.S. Pat. No. 4,391,802; Suda et al. Proc. Natl. Acad. USA 80, 201 (1983); Reitsma et al., Nature, 306, 492–494 (1983)].

Most of the known vitamin D metabolites and analogs are derivatives of the vitamin $D_3$ series, i.e. they possess saturated steroid side chains. Side chain unsaturated vitamin D compounds are, however, also known, namely certain hydroxyderivaties of vitamin $D_2$ such as 25-hydroxyvitamin $D_2$ (U.S. Pat. No. 3,585,221), 1α,25-dihydroxyvitamin $D_2$ (U.S. Pat. No. 3,880,894), the 24-hydroxy- and 24,25-hydroxyvitamin $D_2$ metabolites (Jones et al., Arch. Biochem. Biophys. 202, 450 (1980), 1α-hydroxyvitamin $D_2$ (U.S. Pat. No. 3,907,843), as well as certain related 22-trans-dehydro compounds lacking the 24-methyl substituent as described in U.S. Pat. No. 3,786,062 and by Bogoslovskii et al. (J. Gen. Chem. USSR 48(4), 828 (1978); Chem. Abstr. 89, 163848j, 89, 209016s).

DISCLOSURE OF INVENTION

Novel vitamin D analogs have now been prepared which are characterized by the structure:

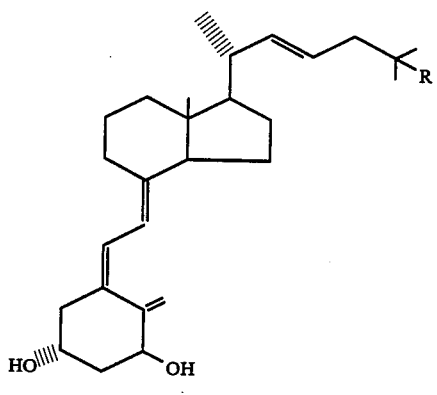

wherein R is hydrogen or a hydroxy group. The compound of this invention wherein R is hydrogen can be obtained as an intermediate in the preparation of the compound where R is hydroxy.

Structurally the compounds of this invention are analogs of hydroxyvitamin $D_2$ compounds which lack the 24-methyl substituent, i.e. the compounds are 1α-hydroxy-28-norvitamin $D_2$ and 1α,25-dihydroxy-28-norvitamin $D_2$, respectively.

Both the product and the intermediate exhibit high biological activity and are characterized by an unexpected and novel pattern of activity as further described below.

An embodiment of the chemical process leading to the above named compounds is depicted in Process Scheme I. In the following description of this process, and in the Examples and Tables, compound designations by Arabic Numerals (e.g. (1), (2), (3), ... (10), (11), (12)) refer to the structures so number in the Process Scheme.

The starting material is the diene-protected aldehyde of structure (1) (see Process Scheme I), which is prepared from ergosterol acetate according to the method of Barton et al. (J. Chem. Soc. (C) 1968 (1971)). Reaction of aldehyde (1) with 3-methyl-1-butylphenylsulfone having the structure shown below:

$(CH_3)_2CHCH_2CH_2—SO_2Ph$ in an organic solvent and in the presence of a strong organic base gives the hydroxy-sulfone intermediate of structure (2), as shown in Process Scheme I. Treatment of intermediate (2) with sodium amalgam in buffered alcohol solution then provide the 22,23-trans olefin (22E-olefin) of structure (3).

Reaction of the 22E-olefin (3) with a strong hydride reducing reagent (e.g. LiAlH₄) in an ether solvent gives the 5,7-diene intermediate (4). This intermediate is then irradiated with ultraviolet light in an organic solvent to obtain the corresponding previtamin D derivative, which is isolated and heated in an organic solvent at a temperature ranging from room temperature to reflux to isomerize the previtamin D chromophore to the vitamin D chromophore, thus affording the 22E-dehydrovitamin $D_3$ compound of stucture (5). Compound (5) is a known vitamin D analog, having been prepared previously by a less convenient method (Bogoslovskii et al., supra).

Intermediate (5) is then hydroxylated at carbon 1, according to the general procedure of DeLuca et al. (U.S. Pat. Nos. 4,195,027 and 4,260,549). These reaction steps involve the reaction of compound (5) with toluenesulfonyl chloride in the conventional manner to obtain the corresponding 3β-tosylate derivative which is directly solvolyzed in buffered methanol to obtain the 3,5-cyclovitamin D intermediate represented by structure (6) in Process Scheme I. By treatment of the latter with selenium dioxide and tert.-butyl hydroperoxide, there is obtained after chromatographic purification the corresponding 1-hydroxylated product comprising chiefly the 1α-hydroxycyclovitamin D compound of structure (7). A small amount of the corresponding 1α-hydroxy epimer may also be present in the product, but separation of the epimers, though possible by chromatography is not necessary at this stage. Heating of this 1-hydroxycyclovitamin D intermediate in glacial acetic acid at 40°-60° C. then provides a mixture of the 3-acetylated solvolysis products from which are isolated by chromatography the 5,6-cis and 5,6-trans compounds of structures (8) and (9), respectively. If the 1-hydroxycyclovitamin D product subjected to solvolysis contained some 1β-hydroxy-epimer, then the solvolysis mixture will contain also the 1β-hydroxy epimers corresponding to compounds (8) or (9) and, if desired, these can also be isolated by chromatography.

Conventional base hydrolysis of the acetate function in compound (8) yields the diol product of structure (10).

This (10) is then subjected to in vitro enzymatic hydroxylation at carbon 25, using a liver homogenate prepared from vitamin D-deficient rats, (as described in U.S. Pat. No. 4,307,025) to obtain, after chromatographic separation of the product mixture, then desired 1α,25-dihydroxylated product, represented by structure (12), in pure form.

In the following detailed description of the synthetic process outlined above the physiochemical data was obtained using the below referenced methods and apparatus. High pressure liquid chromatography (HPLC) was performed on a Waters Associates Model ALC/GPC 204 using a Zorbax-Sil (Dupont) column (6.2 mm×25 cm column, flow rate 4 ml/min, 1500 psi). Column chromatography was performed on Silica Gel 60, 70–230 mesh ASTM (merck). Preparative thin-layer chromatography (TLC) was carried out on Solica 60 PF-254 (20×20 cm plates, 1 mm silica gel). Irradiations were carried out using a Hanovia 608A36 mercury arc lamp fitted with a Vycor filter. All reactions are preferably performed under an inert atmosphere (e.g. argon).

3-Methyl-l-butylphenylsulfone (Isopentylphenylsulfone) PhSO$_2$Na (1.97 g, 12 mmol) was added to a stirred solution of 3-methyl-l-bromobutane (1.51 g, 1.2 ml, 10 mmol) in DMF (20 ml) at 75° C. The mixture was heated at 75° C. for 5 h, then cooled, poured into water and extracted with benzene. The organic layer was washed with 5% HCl, 5% NaHCO$_3$ and water, dried over Na$_2$SO$_4$ and evaporated. The oily sulfone product (1.69 g. 80%) was substantially pure and used used without any purification; NMR δ 0.88 (6H, d, J=6.5 Hz, 2xHC$_3$), 1.61 (3H, m, —CH$_2$—CH), 3.08 (2H, m, SO$_2$—CH$_2$—), 7.50–7.95 (5H, m, Ar—$\underline{H}$); IR: 1300 (br), 1147,1088,745,692,564,539 cm$^{-1}$; mass spectrum, m/e 212 (M$^+$, 3), 143 (92), 77 (57), 71 (73), 70 (73), 55 (42), 43 (100), 41 (47).

(22E)-5α,8α-(4-phenyl-1-1,2-urazolo)-cholesta-6,22-diene-3β-ol (3) n-Butyllithium (1.7 M solution in hexane, 4.12 ml, 7 mmol) was added to a stirred solution of di-isopropylamine (707 mg, 1 ml, 7 mmol) in dry THF (14 ml) and the mixture was stirred for 15 min at room temperature. The sulfone as prepared in Example 1 (1.50 g, 7.07 mmol) in dry THF (11 ml) was added dropwise in 10 min. The solution was stirred at room temperature for an additional 15 min, then cooled to 0° C. and aldehyde (1) (545 mg, 1 mmol) in dry THF (7 ml) was added. The stirring was continued for 2 h at 0° C. and solution was slowly warmed to room temperature (30 min)). The mixture (containing hydroxy-sulfone product (2)) was poured into saturated solution of Na$_2$HPO$_4$ in methanol (200 ml)), sodium amalgam (5.65%, 10 g) was added and the reaction mixture was stirred at 4° C. for 17 h. Precipitated mercury was filtered off and after concentration of the reaction mixture to 5 ml, it was diluted with water and extracted with methylene chloride. Organic extract was washed with water, dried (Na$_2$SO$_4$), concentrated in vacuo and the oily residue was chromatographed on solica gel column. Excess of sulfone reagent was eluted with benzene-ether (7:3) mixture. Elution with benzene ether (6:4) afforded purre adduct (3) (375 mg, 67%) as a foam: NMR δ 0.81 (3H, s, 18-H$_3$), 0.86 (6H, d, J=6.7 Hz, 26-H$_3$ and 27-H$_3$), 0.97 (3H, s, 19-H$_3$), 1.03 (3H, d, J=6.8 Hz, 21-H$_3$), 3.16 (1H, dd, J$_1$=4.4 Hz, J$_2$=14 Hz, 9-H), 4.44 (1H, m, 3-H), 5.25 (2H, br m, 22-H and 23-H), 6.22 and 6.39 (2H, AB q, J=8.5 Hz, 6-H and 7-H), 7.40 (5H, br m, Ar-H); IR: 3444, 1754,1701,1599,1402,969,757 cm$^{-1}$; mass spectrum, m/e 557 (M$_+$, 1%), 382 (70), 349 (51), 253 (28), 251 (45), 119 (PhNCO, 83), 55 (100).

(22E)-Cholesta-5,7,22-trien-3α-ol (4)

The adduct (3) (330 mg, 0.6 mmol) and lithium alumium hydride (700 mg) in dry THF (40 ml) was heated under reflux for 18 h. The excess of reagent was decomposed with a few drops of water. Anhydrous Na$_2$SO$_4$ was added and the organic phase was decanted and evaporated to give crystalline residue which was purified on a column of solica gel. Elution with benzene ether (94:6) mixture gave pure diene (4) (180 mg, 80%) which was crystallized from methanol: mp 119.5°–122.5° C.; [α]$_D^{24}$=−118° (c=1.2, CHCl$_3$); NMR δ 0.63 (3H, s, 18-H$_3$), 0.87 (6H, d, J=6.7 Hz, 26-H$_3$ and 27-H$_3$), 0.95 (3H, s, 19-H$_3$), 1.03 (3H, d, J=6.8 Hz, 21-H$_3$), 3.64 (1H, m, 3-H), 5.25 (2H, br m, 22-H and 23-H), 5.38 and 5.57 (2H, AB q, J=6 Hz, 7-H and 6-H); UV λ$_{max}$ 281 mm; IR: 3436,1461,1382,1366,1062,1036,968 cm$^{-1}$; mass spectrum, m/e 382 (M$^+$, 100), 349 (M$^+$-H$_2$O-Me, 71), 323 (34), 271 (M$^+$-side chain, 16), 253 (M$^+$-side chain-H$_2$O, 32).

(5Z,7E,22E)-9,10-Secocholesta-5,7,10(19),22-tetraen-3α-ol (5) A solution of compound (4) (100 mg, 0.26 mmol) in ether (120 ml)-benzene (30 ml) mixture was degassed with argon for 40 min. The solution was irradiated at 0° C. for 13 min in a quartz immersion well equipped with UV lamp and filter. The solvent was removed under reduced pressure and the residue separated by HPLC, using 1% 2-propanol in hexane as eluent to obtain the pure previtamin D derivative (40.4 mg, 40%) which was collected at 24 ml; NMR δ 0.72 (3H, s, 18-H$_3$), 0.87 (6H, d, J=6.7 Hz, 26-H$_3$ and 27-H$_3$), 1.04 (3H, d, J=6.8 Hz, 21-H$_3$), 1.65 (3H, s, 19-H$_3$), 3.91 (1H, m, 3-H), 5.28 (2H, br m, 22-H and 23-H, 5.50 (1H, m, 11-H), 5.69 and 5.96 (2H, AB q, J=12.5 Hz, 7-H and 6-H); UV λ$_{max}$ 260.5 nm; λ$_{min}$ 234 nm. The previtamin (40 mg, 0.1 mmol) in ethanol (100 ml) was heated under reflux for 3 h. After removal of solvent, the product mixture was separated by HPLC (elution with 1% 2-propanol in hexane). The yield of the vitamin (5) (collected at 34 ml) was 30.8 mg (77%) mp (hexane) 99°-101° C.; NMR δ 0.56 (3H, s, 18-H$_3$), 0.88 (6H, d, J=6.7 Hz, 26-H$_3$ and 27-H$_3$), 1.02 (3H, d, J=6.6 Hz, 21-H$_3$), 3.96 (1H, m, 3-H), 4.82 and 5.05 (2H, each narr. m, 19-H$_2$), 5.27 (2H, br m, 22-H and 23-H), 6.03 and 6.24 (2H, ABq, J=11.4 Hz, 7-H and 6-H; UV λ$_{max}$ 265 nm, λ$_{min}$ 228 nm; IR: 3420,1458,1441,1378,1366,1050,970,943,891,862 cm$^{-1}$; mass spectrum, m/e (M+, 22), 349 (M+-H$_2$O-Me, 4), 271 (M+-side chain, 8), 253 (M+-side chain-H$_2$O, 13), 136 (100), 118 (80).

(5Z,7E,22E)-3β-Acetoxy-9,10-secocholesta-5,7,10(19)-tetraen-1α-ol (8).

A freshly recrystallized p-toluenesulfonyl chloride (50 mg, 0.26 mmol) was added to a solution of vitamin (5) (30 mg, 0.08 mmol) in dry pyridine (300 µl). After 30 h at 4° C., the reaction mixture was poured into ice/saturated NaHCO$_3$ with stirring. The mixture was stirred for 15 min and extracted with benzene. The organic extract was washed with saturated NaHCO$_3$, saturated copper sulfate and water, dried (Na$_2$SO$_4$) and concentrated in vacuo to obtain the oily 3β-tosyl derivative. The crude tosylate was treated with NaHCO$_3$ (150 mg) in anhydrous methanol (10 ml) and the mixture was stirred for 8.5 h at 55° C. After cooling and concentration to 2 ml the mixture was diluted with benzene (80 ml), washed with water, dried (Na$_2$SO$_4$) and evaporated under reduced pressure. The resulting oily, 3,5-cyclovitamin D analog (6) was sufficiently pure to be used for the following oxidation step without any purification. To a vigorously stirred suspension of SeO$_2$ (4 mg, 0.036 mmol) in dry CH$_2$Cl$_2$ (5 ml), tert.-butylhydroperoxide (13.2 µl, 0.094 mmol) was added. After 30 min day dry pyridine (40 µl) was added and the mixture was stirred for additional 25 min at room temperature, diluted with CH$_2$Cl$_2$ (3 ml) and cooled to 0° C. The crude 3,5-cyclovitamin product (6) in CH$_2$Cl$_2$ (4.5 ml) was then added and the reaction permitted to proceed at 0° C. for 15 min. The mixture was then allowed to warm slowly (30 min) to room temperature. The mixture was transferred to a separatory funnel was shaken with 30 ml of 10% NaOH. Ether (150 ml) was added and the separate organic phase was washed with 10% NaOH, water and dried over Na$_2$SO$_4$. Concentration to dryness in vacuo gave a yellow oily residue which was purified on silica gel TLC plates developed in 7:3 hexane-ethyl acetate (R$_f$0.35) giving 1-hydroxycyclo- vitamin product (14.4 mg, 45%): NMR δ 0.55 (3H, s, 18-H$_3$), 0.64 (1H, m, 3-H), 0.88 (6H, d, J=6.9 Hz, 26-H$_3$ and 27-H$_3$), 1.03 (3H, d, J=6.9 Hz, 21-H$_3$), 3.26 (3H, s, —OCH$_3$), 4.2 (2H, m, 1-H and 6-H), 4.95 (1H, d, J=9.3 Hz, 7-H), 5.1-5.4 (4H, br m, 19-H$_2$, 22-H and 23-H); mass spectrum, m/e 412 (M+, 27), 380 (M+-MeOH, 46), 339 (22), 269 (M+-side chain-MeOH, 29), 245 (18), 135 (100). The above product comprised chiefly the 1α-hydroxycyclovitamin D analog of structure (7) and a small amount of the corresponding 1β-epimer. A solution of this 1-hydroxyclovitamin D product (12 mg) in glacial acetic acid (0.5 ml) was heated at 55° C. for 15 min. The mixture was carefully poured into ice/saturated NaHCO$_3$ and extracted with benzene and ether. The combined extracts were washed with water, dried (Na$_2$SO$_4$) and evaporated. The resulting product mixture was subjected to HPLC (1.5% 2-propanol in hexane as eluant) to obtain 4.9 mg of compound (8) (eluting at 42 ml) and 3.1 mg of compound (9) (eluting at 50 ml).

Compound (8): NMR δ 0.56, (3H, s, 18-H$_3$), 0.88 (6H, d, J=7.0 Hz, 26-H$_3$ and 27-H$_3$), 1.02 (3H, d, J=6.8 Hz, 21-H$_3$), 2.04 (3H, s, -OCOCH$_3$), 4.41 (1H, m, 1-H), 5.02 (1H, narr. m, 19-H), 5.1-5.4 (4H, br m, 3-, 19-, 22- and 23-H), 6.03 and 6.35 (2H, AB q, J=11.4 Hz, 7-H and 6-H); UV λ$_{max}$ 264 nm, λ$_{min}$ 227.5 nm; mass spectrum m/e 440 (M+, 15), 380 (M+-HOAc, 84), 362 (M+-HOAc-H$_2$O, 9), 269 (M+-side chain-HOAc, 40), 251 (15), 135 (100), 134 (94).

Compound (9): NMR δ 0.57 (3H, s, 18-H$_3$), 0.89 (6H, d, J=7.0 Hz, 26-H$_3$ and 27-H$_3$), 1.03 (3H, d, J=6.8 Hz, 21-H$_3$), 2.04 (3H, s, —OCOCH$_3$), 4.49 (1H, m, 1-H), 5.00 and 5.14 (2H, each narr. m, 19-H$_2$), 5.25 (3H, br m, 3-, 22- and 23-H), 5.81 and 6.58 (2H, AB q, J=12.0 Hz, 7-H and 6-H); UV λ$_{max}$ 269.5 nm; λ$_{min}$ 228 nm; mass spectrum, m/e 440 (m+, 6), 380 (47), 269 (15), 135 (100), 134 (62).

Also obtained from the solvolysis product mixture was a small amount (0.87 mg of the 1α-hydroxy-epimer corresponding to compound (8), characterized by the following data: NMR δ 0.55 (3H, s, 18-H$_3$), 0.87 (6H, d, J=6.9 Hz, 26-H$_3$ and 27-H$_3$), 1.01 (3H, d, J=6.9 Hz, 21-H$_3$), 2.06 (3H, s, —OCOCH$_{3}$), 4.17 (1H, m, 1-H), 4.99 (2H, m, 3-H and 19-H), 5.1-5.4 (3H, br m, 19-, 22- and 23-H), 6.00 and 6.38 (2H, AB q, J=11.3 Hz, 7-H and 6-H); UV λ$_{max}$ 262.5 nm, λ$_{min}$ 227 nm; mass spectrum, m/e 44Φ (M+, 27), 380 (78), 362 (12), 269 (28), 251 (20), 135 (100), 134 (78).

Hydrolysis of 3α-acetoxy group in compounds (8) and (9)

A solution of the 3α-acetoxyvitamin derivative (8) (0.7-6 mg) in ethanol (0.1 ml) was treated with 10% KOH in methanol (0.8 ml) and the mixture was heated or 1 h at 50° C. After usual work-up and final HPLC purification (8% 2-propanol in hexane as eluent), there was obtained the 1α,3β-diol of structure (10) in 84% yield: NMR δ 0.56 (3H, s, 18-H$_3$), 0.87 (6H, d, J=7.0 Hz, 26-H$_3$ and 27-H$_3$), 1.02 (3H, d, J=6.8 Hz, 21-H$_3$), 4.22 (1H, m, 3-H), 4.42 (1H, m, 1-H), 5.00 (1H, narr. m, 19-H), 5.1–5.4 (3H, br m, 19-, 22- and 23-H), 6.01 and 6.38 (2H, AB q, J=11.4 Hz, 7-H and 6-H); UV λ$_{max}$ 264.5 nm, λ$_{min}$ 227.5 nm; mass spectrum, m/e 398 (M$^+$, 21), 380 (M$^+$-H$_2$O, 9), 2.87 (M$^+$-side chain, 6), 269 (M$^+$-side chain-H$_2$O, 8), 251 (5), 152 (38), 134 (100). Compound (10) elutes at 40 ml in the above HPLC system.

Analogous treatment of the acetoxy derivative (9), gave after HPLC purification the 5,6-trans-1α,3β-diol of structure (11) in 72% yield: NMR δ 0.58 (3H, s, 18-H$_3$), 0.87 (6H, d, J=7.0 Hz, 26-H$_3$ and 27-H3), 1.03 (3H, d, J=6.8 Hz, 21-H$_3$), 4.24 (1H, m, 3-H), 4.49 (1H, m, 1-H), 4.97 and 5.13 (2H, each narr. m, 19-H$_2$), 5.25 (2H, br m, 22-H and 23-H), 5.88 and 6.58 (2H, AB q, J=11.5 Hz, 7-H and 6-H); UV λ$_{max}$ 273 nm, λ$_{min}$ 229.5 nm, mass spectrum, m/e 398 (M$^+$, 21), 380 (5), 287 (6), 269 (5), 251 (4), 152 (33), 134 (100). Compound (11) elutes at 38 ml.

25-Hydroxylation of compound (10)

The 5,6-cis-1α,3β-diol of structure (10) as obtained in above was then 25-hydroxylated by the following procedure: Male weanling rats were fed a low calcium vitamin D-deficient diet as described by Suda et al. J. Nutr. 100, 1049 (1970) for 2 weeks. They were killed by decapitation and their livers were removed. A 20% (w/v) homogenate was prepared in ice-cold 0.25 M surcrose. Incubation was carried out in 10 ml incubation medium in a 125 ml Erlenmayer flask containing an aliquot of liver homogenate representing 1 g of tissue, 0.125 M sucrose, 50 mM phosphate buffer (pH 7.4), 22.4 mM glucose-6-phosphate, 20 m ATP, 160 mM nicotinamide, 25 mM succinate, 0.4 mM NADP, 5 mM MgCl$_2$, 0.1 M KCl and 0.5 units glucose-6-phosphatedehydrogenase. The reaction was initiated by addition of 400 μg of compound (10) dissolved in 100 μl 95% ethanol. The mixture was incubated at 37° C. with shaking at 80 oscillations/min for 3 h. The reaction was stopped by the addition of 20 ml methanol and 10 ml dichloromethane. After further addition of 10 ml dichloromethane, the organic phase was collected while aqueous phase was re-extracted with 10 ml dichloromethane. The organic phases from total of three extractions were combined and evaporated with a rotary evaporator. The residue containing the desired product was dissolved in 1 ml of CHCl$_3$:Hexane (65:35) mixture and applied to a Sephadex LH-20 column (0.7 cm×14 cm) packed, equilibrated and eluted with the same solvent. The first 10 ml was discarded while the next 40 ml was collected and evaporated. The residue was then dissolved in 8% 2-propanol in hexane and subjected to high performance liquid chromatography (Model LC/GPC 204 HPLC, Waters Associates, Medford, MA) using a Zorbax-Sil column (4.6 nm×25 cm, Dupont, Inc., Wilmington, Del.) operating under pressure of 1000 psi with a flow rate of 2 ml/min. The desired 25-hydroxylated product was eluted at 42 ml. The product was further purified by high performance liquid chromatography using a reverse phase column (Richrosorb Rp-18, 4.6 mm×35 cm, E. Merck, Darmstadt, West Germany) operated under pressure of 1200 psi and a flow rate of 2 ml/min. The column was eluated with 22% H$_2$O in methanol and the product was eluted at 50 ml. The product was further purified by HPLC using Zorbax-Sil and conditions as described above. The resulting product was characterized by the following data: UV absorption (95% ethanol) λ$_{max}$ 265 nm, λ$_{min}$ 228 nm; mass spectrum, m/z 414 (mol. ion M$^+$), 396 (M$^+$-H$_2$O), 378 (M$^+$-2xH$_2$O), 287 (M$^+$-side chain), 269 (M$^+$-side chain-H$_2$O), 251 (M$^+$-side chain-2xH$_2$O), 152 (ring A, C 7/8 bond cleavage), 134 (152-H$_2$O) and 59 ((CH$_3$)$_2$C=OH)$^+$ resulting from C24/25-bond cleavage).

The above data, especially the characteristics ultraviolet absorption and the prominent and diagnostic peaks at m/z 152, 134 and 59 in the mass spectrum, establish the product to be the desired 25-hydroxylated compound represented by structure (12) (Process Scheme I).

If desired, the compounds of this invention can be readily obtained in crystalline form by crystallization from suitable solvents, e.g. hexane, ethers, alcohols, or mixtures thereof, as will be apparent to those skilled in the art.

BIOLOGICAL ACTIVITY OF SIDE CHAIN DEHYDROVITAMIN D COMPOUNDS

The biological potency of the above described dehydrovitamin D analogs was established by in vivo assays in the rat and comparison with 1α-hydroxyvitamin D compounds of known potency. Both product (12) and the key intermediate, compound (10) were teated and found to be highly active.

BIOLOGICAL ACTIVITY OF COMPOUND (10)

The assay was conducted as follows: Male weanling rats were purchased from Holtzman Co., Madison, WI and fed ad libtum water and a low calcium-adequate phosphorus, vitamin D-deficient diet as described by Suda et al. (J. Nutr. 100, 1049 (1970)) for three weeks. Rats were then divided into groups of 6 rats each and were given 650 pmol of either compound (10) or 1α-hydroxyvitamin D$_3$ (1α-OH-D$_3$) dissolved in 0.05 ml 95% ethanol intrajugularly 18 h prior to sacrifice. The rats in the control group were given ethanol vehicle in the same manner. The rats were killed by decapitation and the blood was collected. Serum obtained by centrifugation of the blood was diluted with 0.1% lanthanum chloride solution (1:20) and serum calcium concentration was measured with an atomic absorption spectrophotometer. Results are shown in the Table I below:

TABLE 1

| Increase in serum calcium concentration in response to a single dose of 650 pmol of either compound (10) or or 1α-OH-D$_3$, given 18 h prior to sacrifice | |
|---|---|
| Compound Given | Serum Calcium Concentration (mg/100 ml) ± Standard Deviation |
| ethanol | 3.2 ± 0.1[a] |
| compound (10) | 4.5 ± 0.4[b] |
| 1α-OH-D$_3$ | 4.7 ± 0.5[b] |

[b]is significantly different from[a] p 0.001.

BIOLOGICAL ACTIVITY OF COMPOUND (12)

The assay was performed as follows: Male weanling rats were fed a low calcium vitamin D-deficient diet for 3 weeks as described above. They were the divided into groups of 5 rats each. Rats in a control group received 0.05 ml 95% ethanol intrajugularly while rats in the test groups were given 325 pmol of either compound (12) or of $1\alpha,25$-dihydroxyvitamin $D_3$ ($1\alpha,25$-$(OH)_2D_3$) dissolved in 0.05 ml 95% ethanol. Eighteen hours later they were killed by decapitation and blood was collected. Serum calcium concentration was determined with an atomic absorption spectrophotometer as described above. Results are shown in Table II below:

TABLE II

Increase in serum calcium concentration in response to single dose of 325 pmol of either compound (12) or $1\alpha,25$-$(OH)_2D_3$ given 18 h prior to sacrifice

| Compound Given | Serum Calcium Concentration (mg/100 ml) + Standard Deviation |
| --- | --- |
| ethanol | $4.2 \pm 0.1^{(a)}$ |
| compound (12) | $5.0 \pm 0.4^{(b)}$ |
| $1\alpha,25$-$(OH)_2D_3$ | $5.4 \pm 0.4^{(b)}$ |

$^{(b)}$is significantly different from$^{(a)}$ p 0.001.

The above results show that both compound (10) and the final product (12) of this invention are highly active in promoting a rise in serum calcium levels of vitamin D-deficient rats. They are, in fact, equivalent in biological potency to the corresponding known side chain-saturated compounds, $1\alpha$-OH-$D_3$ $1\alpha,25$-$(OH)_2D_3$, the high potency and pharmaceutical utility of which is well documented by many reports in the general and patent literature (e.g. see U.S. Pat. No. 4,225,596.

Particularly noteworthy and unexpected is the superior activity of compound (10) in mineralizing the bones of an animal (chick) that discriminates against the physiological utilization of the vitamin $D_2$ compounds. This is amply illustrated by the following data.

METHOD

Day-old white Leghorn male chicks were obtained from Northern Hatcheries (Beaver Dam, Wis.). They were fed the vitamin D-deficient soy protein diet described in Omdahl et al (Biochemistry 10, 2935–2940, 1971) for 3 weeks at which time they were vitamin D deficient. They were then divided intto groups of 6 chicks each. One group received Wesson oil vehicle by mouth; the other groups received the indicated compounds (see Table III) dissolved in the same amount of Wesson oil each day for 7 days. Twenty-four hours after the late dose, all chicks were killed by cervical dislocation. Their tibiae were removed and freed of adherent soft and connective tissue and extracted for 24 hours in alcohol followed by 24 hours in diethyl ether using a Soxhlet extractor. The bones were then dried to constant weight at 100° F. and weighed. They were then ashed at 650° C. for 24 hours in a muffle furnace. The ash was weighed and the percent ash in each of the tibiae was calculated. Results are shown in Table III below.

TABLE III

Mineralization of Rachitic Chick Bone

| Compound | Amount (pmole/d/7 days) | Number of Animals | % Ash |
| --- | --- | --- | --- |
| -D | 0 | 6 | $32.0 \pm 1.0$ |
| $1,25$-$(OH)_2D_3$ | 130 | 6 | $41.0 \pm 3.4$* |
| $1\alpha$-OH-$D_3$ | 130 | 6 | $42.0 \pm 3.2$* |
| $1\alpha$-OH-$D_2$ | 1300 | 6 | $38.0 \pm 4.0$* |
| Compound (10) | 130 | 6 | $38.0 \pm 3.9$* |

*These values are not significantly different

The results demonstrate that 130 pmoles of either $1,25$-$(OH)_2D_3$ or $1\alpha$-OH-$D_3$ or the novel compound (10) of this invention, were equally effective in increasing the mineral content of the rachitec tibia. However, to achieve the same degree of effectiveness, 1300 pmoles of $1\alpha$-OH-$D_2$ was required. This agrees with previous results in which it was shown that a 10-fold greater dose of $1\alpha$-OH-$D_2$ than $1\alpha$-OH-$D_3$ is required to produce the same mineralization of the tibia of rachitic chickens. These results demonstrate, surprisingly, that although compound (10) is an analog of $1\alpha$-OH-$D_2$, it offers unexpected and superior activity in mineralizing the bones of an animal that is known to discriminate against the vitamin $D_2$ compounds in physiological utilization. This is an unexpected characteristic of and utility for this new analog. Since the unexpected in vivo activity of compound (10) is undoubtedly manifested after hydroxylation to the corresponding $1\alpha,25$-dihydroxy compound (compound (12)) in vivo, that compound, i.e. compound (12), which is the 24-desmethyl analog of the known $1\alpha,25$-dihydroxyvitamin $D_3$, should function to provide bone mineralization in chicks equivalent to that shown by $1\alpha,25$-dihydroxyvitamin $D_3$; thus this novel vitamin $D_2$ analog would be fully active in the chick. This high potency of compounds (10) and (12) in an animal that discriminates against vitamin $D_2$-type derivatives, is a novel and distinctive characteristics of these substances.

Because of this marked biological activity, the compounds of this invention will find ready application as substitutes for various of the known vitamin D metabolites in the therapy or prophylaxis of calcium metabolism disorders such as rickets, hypoparathyroidism, osteodystrophy, osteomalacia or osteoporosis in the human, or related calcium deficiency diseases (e.g. milk fever) in animals. Likewise, these compounds may be used for the treatment of certain malignancies, such as human leukemia. In view of the marked and unexpected activity of the compounds of this invention (compounds (10) and (12)) in promoting the mineralization of bone in birds (see Table III), these compounds would have particular utility in the prevention or treatment of calcium imbalance-induced conditions (e.g. egg shell thinness, poultry leg weakness) in poultry where all the known vitamin $D_2$ derivatives exhibit very poor activity.

For therapeutic purposes, the compounds may be administered by an conventional route of administration and in any form suitable for the method of administration selected. The compounds may be formulated with any acceptable and innocuous pharmaceutical carrier, in the form of pills, tablets, gelatin capsules, or suppositories, or as solutions, emulsions, dispersions or suspensions in innocuous solvents or oils, and such formulation may contain also other therapeutically active and beneficial ingredients as may be appropriate for the specific applications. For human applications, the compounds are advantageously administered in amounts from 0.5 to 10 μg per day, the specific dosage being adjusted in accordance with the specific compound administered, the disease treated and the conditions and response of the subject, as is well understood by those skilled in the art.

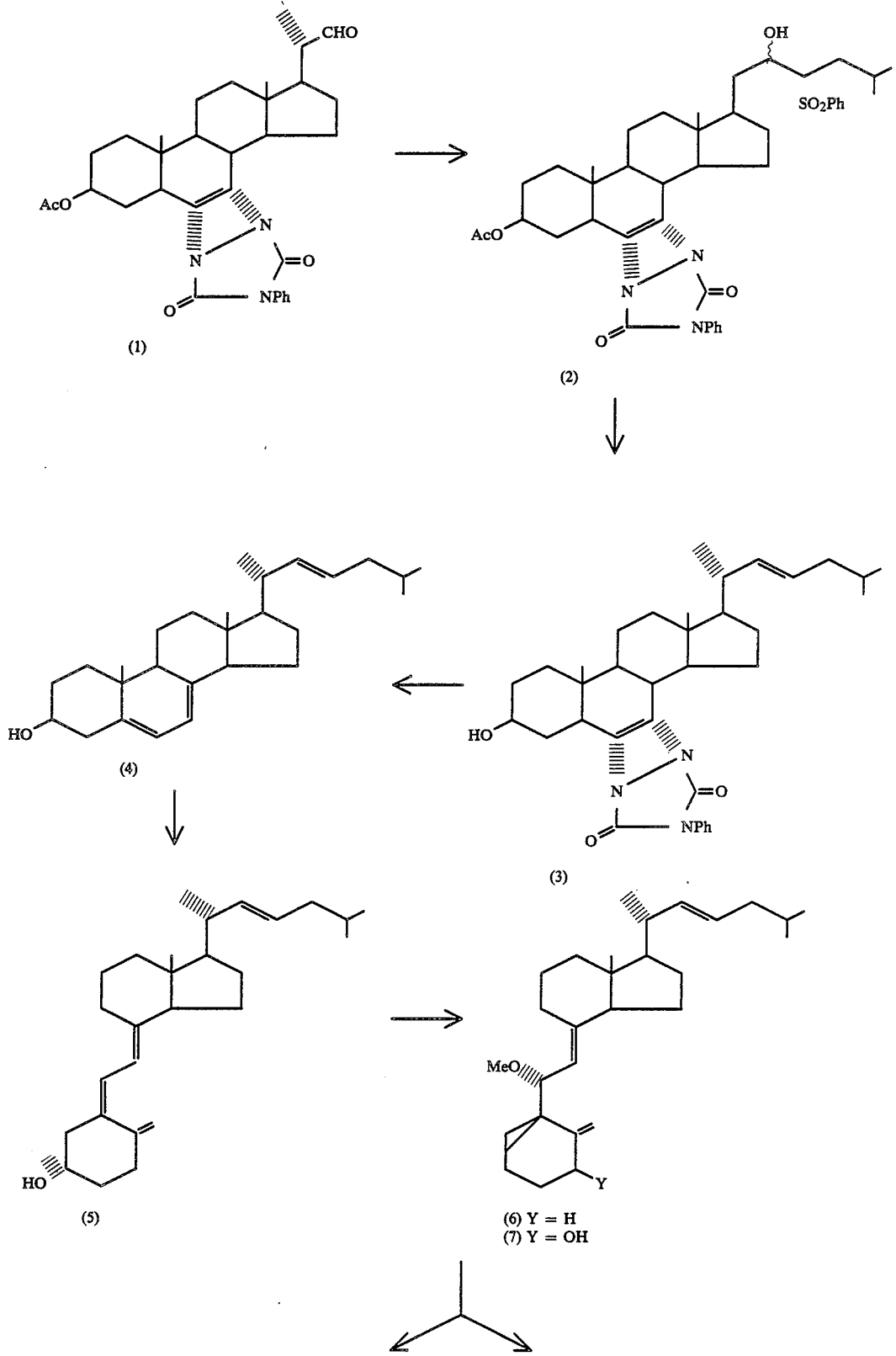

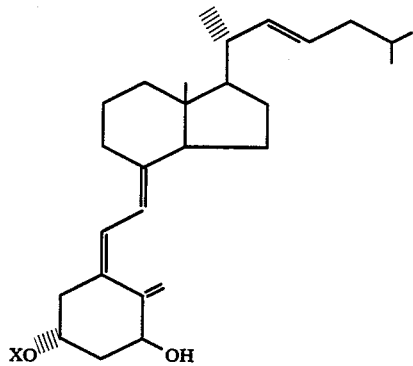

(8) X = Ac
(10) X = H

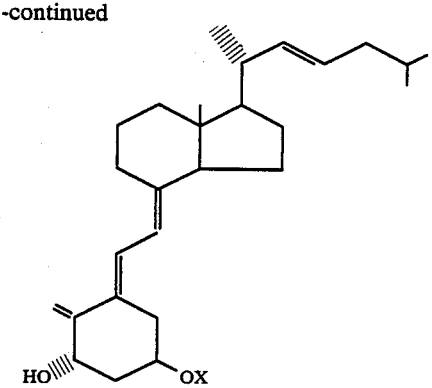

(9) X = Ac
(11) X = H

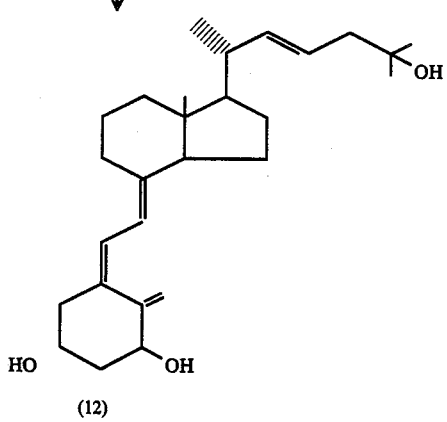

(12)

We claim:
1. A method for inducing the mineralization of the bones of fowl which comprises administering to said fowl an effective amount of 1α-hydroxy-28-norvitamin D₂ or 1α, 25-dihydroxy-28-norvitamin D₂.

2. The method of claim 1 wherein the said compound is administered in admixture with feed.
3. The method of claim 2 wherein the said compound is dissolved in an appropriate solvent innocuous to said fowel and sprayed on said feed.

* * * * *

UNITED STATES PATENT OFFICE
CERTIFICATE OF CORRECTION

Patent No. 4,719,204           Dated  January 12, 1988

Inventor(s) DeLuca, Schnoes, Sicinski, Tanaka

It is certified that error appears in the above-identified patent and that said Letters Patent are hereby corrected as shown below:

In Process Scheme I, columns 11 & 12, change from:

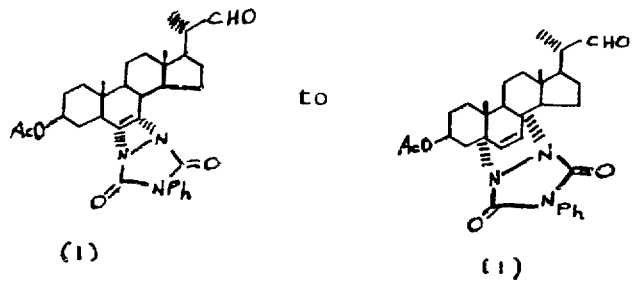

In Process Scheme I, columns 11 & 12, change from:

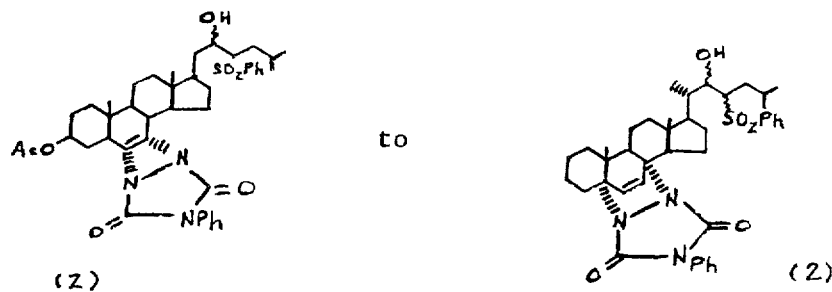

In Process Scheme I, columns 11 & 12, change from:

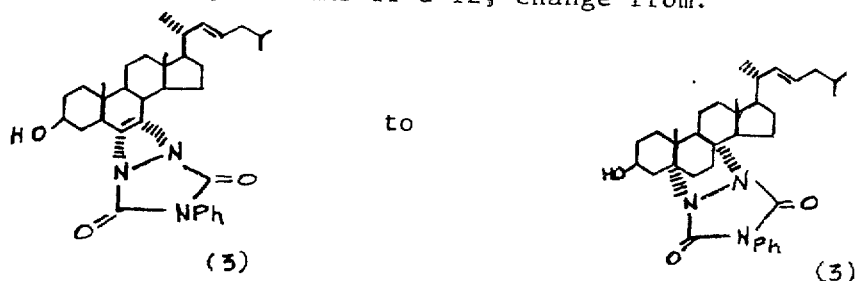

UNITED STATES PATENT OFFICE
CERTIFICATE OF CORRECTION

Patent No. 4,719,204　　　　　　　　　　Dated January 12, 1988

Inventor(s) DeLuca, Schnoes, Sicinski, Tanaka

It is certified that error appears in the above-identified patent and that said Letters Patent are hereby corrected as shown below:

In Process Scheme I, Columns 11 & 12, change from:

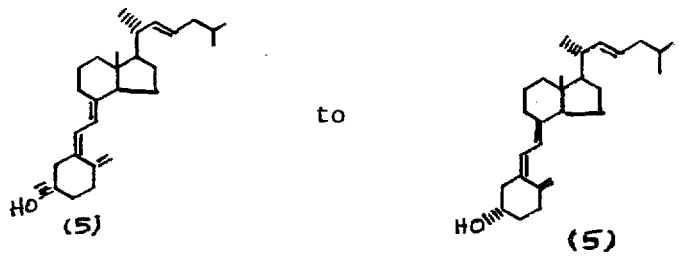

In Process Scheme I, columns 11 & 12, change from:

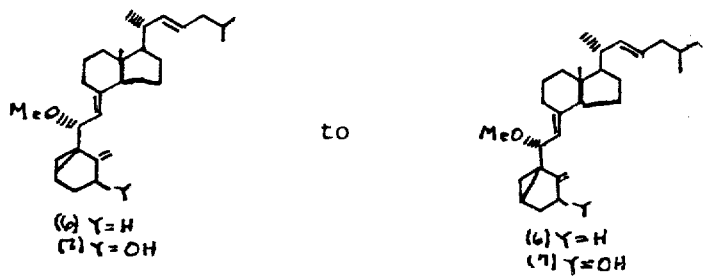

UNITED STATES PATENT AND TRADEMARK OFFICE
CERTIFICATE OF CORRECTION

PATENT NO. : 4,719,204
DATED : January 12, 1988
INVENTOR(S) : Deluca, Schnoes, Sicinski, Tanaka It is certified that error appears in the above-identified patent and that said Letters Patent is hereby corrected as shown below:

In Process Scheme I, column 13, second structure, change from:

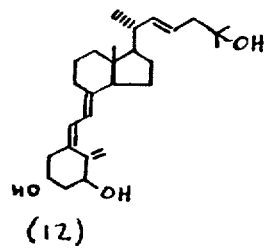 to 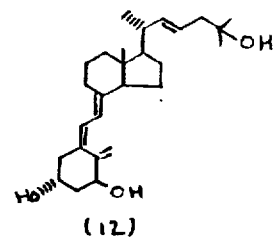

Signed and Sealed this

Eighteenth Day of October, 1988

Attest:

DONALD J. QUIGG

Attesting Officer

Commissioner of Patents and Trademarks